United States Patent [19]

O'Brien et al.

[11] Patent Number: 4,566,315
[45] Date of Patent: Jan. 28, 1986

[54] METER FOR MEASURING ERYTHROCYTE SETTLING RATES

[75] Inventors: Robert N. O'Brien; Philip M. McOrmond; Martin B. Hocking; Kenneth R. Thornton, all of Victoria, Canada

[73] Assignee: University of Victoria, Victoria, Canada

[21] Appl. No.: 638,248

[22] Filed: Aug. 6, 1984

Related U.S. Application Data

[63] Continuation-in-part of Ser. No. 389,252, Jun. 17, 1982, Pat. No. 4,474,056.

[30] Foreign Application Priority Data

Aug. 18, 1981 [CA] Canada .................................. 384115

[51] Int. Cl.⁴ ............................................. G01N 15/04
[52] U.S. Cl. ..................................................... 73/61.4
[58] Field of Search ................. 73/61.4; 356/441, 442, 356/337, 338, 39; 346/33 ME

[56] References Cited

U.S. PATENT DOCUMENTS 2,379,158  6/1945  Kalischer .............................. 73/61.4
4,182,161  1/1980  Greenfield ............................ 73/61.4
4,474,056 10/1984  O'Brien et al. ....................... 73/61.4

FOREIGN PATENT DOCUMENTS 916128  8/1954  Fed. Rep. of Germany ....... 73/61.4

Primary Examiner—Stewart J. Levy
Assistant Examiner—Joseph W. Roskos
Attorney, Agent, or Firm—Ezra Sutton

[57] ABSTRACT

A novel meter is provided for measuring erythrocyte settling rates. It includes a base supporting a rack adapted to hold an array of tubes at an optimum settling angle and at least one tube adapted to contain blood samples, the tube including an upper window of predetermined length and a lower window of predetermined length below the upper window and separated therefrom by an opaque section, each window permitting passage of ambient light therethrough. A timer is provided which is actuated by the passage of light through the windows when the tube contains blood, to determine the rate at which the erythrocytes settle. This timing is achieved by means of an upper photodiode behind the upper window actuated by the passage of ambient light through the upper window to begin cumulative time counting, and a lower photodiode behind the lower window actuated by the passage of ambient light through the lower window to stop the cumulative time interval counting, the time interval being representative of the erythrocyte settling rate. Preferably the time interval is displayed. By this invention, a blood test may be done in 5 to 15 minutes. A doctor (or probably his nurse) can perform the test while continuing the examination of the patient and have the results in time for diagnosis.

16 Claims, 4 Drawing Figures

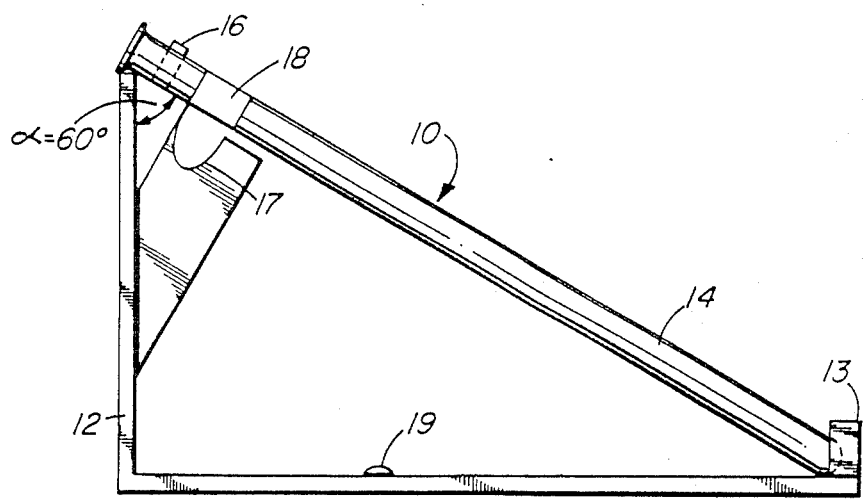
(PRIOR ART) FIG. 1
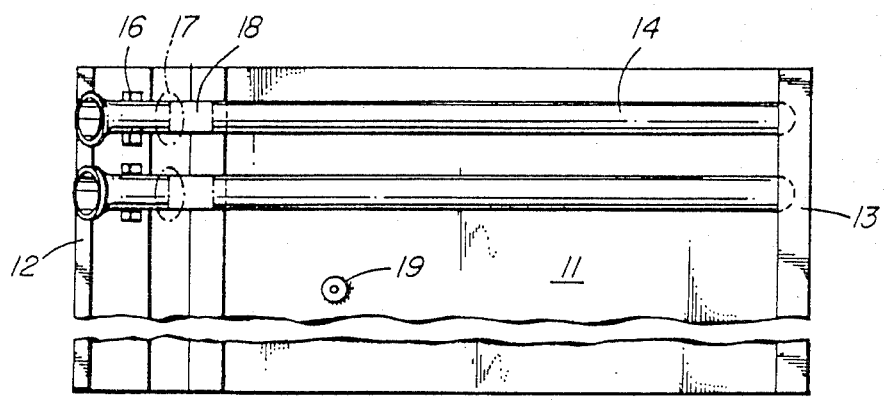
(PRIOR ART) FIG. 2
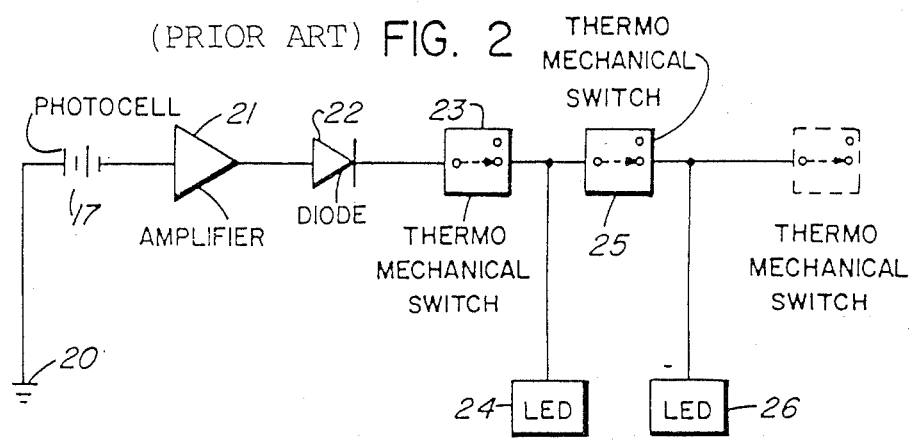
FIG. 3
PRIOR ART

METER FOR MEASURING ERYTHROCYTE SETTLING RATES

RELATED APPLICATIONS

This application is a continuation-in-part of pending application Ser. No. 389,252 filed June 17, 1982, now U.S. Pat. No. 4,474,056.

BACKGROUND OF THE INVENTION (i) Field of the Invention

This invention relates to a meter for measuring the rate at which erythrocytes settle.

(ii) Description of the Prior Art

Measurement of erythrocyte settling rates, usually described as a blood test, is one of the most common medical tests made. When pathogens are present, extra antibodies are secreted and carried in the blood. These are mainly proteins and they cause clumping of red blood cells into rouleaux which are larger than normal and hence settle faster. A blood test shows this, but such test, as presently operated, usually requires two hours for reliable results. In one standard form of blood test, a specific amount of anticoagulant must be used (to prevent clotting during the test) and, to ensure good mixing, a few minutes of shaking of the blood sample is required. Then a sample must be placed in a vertical rack, a timer set and the rate of sedimentation (about 3 mm/hour for healthy humans) observed for one to two hours. Usually the operation is done in a hospital or clinical laboratory. This generally means that, with transportation delays, the results may not be known until the next day.

Other patented proposals have been made in similar and other fields to determine settling rates for solids, or cloud points of liquids or viscosity of liquids.

In the field of blood test machines, German Pat. No. 916,128 dated July 8, 1949 to J. Reppisch provided a blood test machine in which tubes containing blood were held in an incined position, and in which the settling rate was estimated visually by looking straight down into the frame and the sides of the Westergren pipettes used.

U.S. Pat. No. 2,514,260 issued July 4, 1950 to M. S. Rosen provided apparatus for determining the rate of sedimentation of the solid particles in a fluid menstruum, e.g., the erythrocyte sedimentation rate, of any blood-containing sample. The apparatus included a container comprising two parallel circular discs connected at their peripheries by a cylindrical band. The container, when filled with blood, must be maintained vertical. A circular opening was located at one point on the band and a short tube was connected with the opening to facilitate filling of the space between the discs and the band. One face of the disc had indices thereon, to permit reading of volumes of sediment settling within the container.

U.S. Pat. No. 2,528,704 issued Nov. 7, 1950 to P. M. Neuda provided apparatus for determination of the settling rate of erythrocytes. The erythrocyte settling container was of predetermined triangular vertical section which gradually widens from its top to the bottom. The container was disposed so that there was a vertical orientation so that a wide zone of separation of the fluid-solid mixture was provided at the bottom while, simultaneously, both a quick transfer of the plasma through narrowing spaces toward the surface and a subsequent speed sedimentation of the erythrocytes through spaces widening towards the bottom was secured.

U.S. Pat. No. 3,009,352 issued Nov. 21, 1961 to P. M. Neuda provided an improvement in the Neuda triangle of U.S. Pat. No. 2,528,704. The new triangular container was a triangularly shaped flat container, the sides of the triangular being equilateral, with a top aperture, a V-shaped neck outside the triangle, with each side of the V being exactly parallel to the side of the triangle opposite thereof, and a precise scale, on the outside of the triangular container calibrated in desired units.

German Offenlegungsschrift No. 23 24 015 published Nov. 28, 1974 provided a system for measuring the settling speed of erythrocytes in blood by resonant frequency measurement.

Sokal, German Offenlegungsschrift No. 23 41 403 published Feb. 27, 1975 provided a sedimentation test reaction measuring instrument which had a holder for the measuring tube containing the blood. The instrument also had a recording facility. One light source was located at one side of the measuring tube and light beams were transmitted through part of the full length of the measuring tube. On the other side of the measuring tube was arranged a secondary facility which was exposed to light beams. The portion of the light-dark threshold between the blood serum level and the blood corpuscles was recorded. The light source had a grid of horizontal lines and the line elements were at right angles to the vertically positioned measuring tube. The recording facility contained a light sensitive recording strip.

U.S. Pat. No. 3,952,579 patented Apr. 27, 1976 to M. Nakajima provided an improvement in a device for measuring blood sedimentation rates automatically. A light-sensitive paper sheet was disposed so as to be movable relative to a blood sedimentation measuring tube, such as a Westergren tube. A slit was provided between the light-sensitive paper and the measuring tube. Lamp means were provided on one side of the measuring tube opposite to the slit. Thus the shade of the sedimented red blood corpuscles in the measuring tube formed as the light pulsed from the lamp means passing through the measuring tube was projected on the light-sensitive paper through the slit, with the feed of the paper and light pulses occurring in exact synchronism. The rate of the blood sedimentation could be automatically recorded on the paper.

U.S. Pat. No. 4,027,971 patented June 7, 1977 by P. Kolman et al provided an analytical apparatus for counting the quantity of blood fractions. White light, which was directly transmitted through a predetermined volume of the blood, was filtered through a light filter, and light of the selected optical wavelength was passed through.

Heinlein, German Offenlegungsschrift No. 26 31 291 published Jan. 19, 1978 provided a device for the measurement of blood corpuscle sedimentation which had light flux falling on a transducer and enabled its charge to be displayed. A light source and photoelectric transducer were so placed on both sides of a vertical capillary that light flux passed through the capillary and fell on the transducer. An evaluating device was connected to the transducer output, which displayed instantaneous light flux received by the transducer and/or its charge in time.

U.S. Pat. No. 4,187,462 patented Feb. 5, 1980 by R. Haker et al provided a device for determining the blood sedimentation rate in a substantially vertical test tube. The electrical or magnetic property of a given volume of liquid, which was changed by the settling of the erythrocytes in the test tube, was measured as a function of time, by electrical means.

In the more general field of particle rate settling, U.S. Pat. No. 2,379,158 issued June 26, 1945 to P. R. Kalischer et al provided a technique for the determination of the characteristics of the particles in a powdered material using an apparatus including a vertically disposed settling column, a light source and a light sensitive device disposed about the settling column to indicate the relative light transmission through a transparent cross-sectional portion of the column. The light source and light sensitive device were disposed at a sufficient distance from the admission end of the column so that the admitted particles of the powdered material, under the influence of settling forces, underwent a relative gradation resulting in closely similar sized particles being present in any cross-sectional volume of dispersing medium in the settling column when the particles settle past the portion through which light from the light source passed.

U.S. Pat. No. 2,741,913 issued Apr. 17, 1956 to N. Dovau related to racks for holding ungraduated sedimentation tubes against a graduated background. The patented rack was for holding sedimentation tubes beside graduated scales and included a body block member having bottom feet and a central portion supported by and bridging such feet, a front face and a plurality of spaced vertically oriented sedimentation tube openings adjacent the front face. A plurality of spaced graduated scales were provided on the front face adjacent the openings, and a plurality of spring clips were secured to the body block member and were disposed in the openings removably to hold sedimentation tubes therein.

Canadian Pat. No. 912,849 issued Aug. 10, 1972 to P. Cahour et al provided a device for controlling the rate of settlement of a solid in suspension in a liquid involving the use of a settlement cell comprising a vertical, transparent glass column, and a projector for projecting a horizontal beam of light through the column to be picked up by a photoelectric cell which could produce a signal that detected the precise moment when the settling face moved past that level.

U.S. Pat. No. 3,812,966 issued May 28, 1979 to W. A. Beach et al provided a determination of the settling rate of particulate matter by passing a mixture of the fluid and the particulate matter through an inclined tube at a known flow rate within the laminar flow range. Lights were positioned on one side of the inclined tube, and photocells were positioned on the other side. The signals generated thereby could be used to control the operation of a separator.

U.S. Pat. No. 4,182,161 patented Jan. 8, 1980 by W. Greenfield provided a device for automatically timing and recording the sedimentation rate of fluid samples contained in cylindrical transparent test tubes. The device included a rectangular rack having flat vertical walls formed with cylindrical bars for receiving the test tubes, and vertical channels at outer sides of the walls for receiving photographic strips. A lamp inside the rack shone through test tubes to the strips to record the amount of sedimentation of the fluid.

In the realm of non-analogous art, Canadian Pat. No. 715,290 issued Oct. 10, 1965 to P. G. Holdbourne, provided a method for continuously monitoring the cloud point or the pour point of hydrocarbon oil, involving the use of a beam of light which was directed through the oil onto a reflecting surface. The temperature of the oil was measured when the intensity of the beam of light reflected from the reflecting surface decreased a predetermined amount.

U.S. Pat. No. 3,411,352 issued Apr. 29, 1969 to L. A. Hughes provided a colorimeter which included a plurality of photoelectric cells, each having associated with it a light filter which removed all except the particular monochromatic band of light to which the photoelectric cell was primarily responsive and where its peak response was located. Thus, a different cell was used for each colour of light. A receptacle received a colorimeter cuvette containing a specimen, a spring in the cuvette urging it against one side thereof. At one side of the receptacle was an electric lamp as a light source and on the diametrically opposite side, against which the cuvette was urged, were a plurality of vertically displaced photoelectric cells. Each cell had maximum sensitivity to a different monochromatic light and had associated with it a filter for transmitting to the cell that monochromatic light to which its cell had maximum sensitivity. An electric circuit included the lamp, switch means for placing each cell in the circuit, only one at any time, a bridge circuit responsive to the current of the cell then in the circuit, and an electrical heater which operated as an incubator having a plurality of cuvette receptacles. A plurality of interchangeable meters, each relevant to one particular test and calibrated for direct reading in that test in conjunction with one cell and each insertable into and removable from the electric circuit was supplied, but only one was used at a time across the bridge circuit for measuring light transmissivity of the specimen as expressed by the current passing through the photoelectric cell then in the electric circuit. Some of these meters had an actuator and some did not, the actuator, when present, throwing the switch means to place a different cell in the electric circuit.

U.S. Pat. No. 3,071,961 patented Jan. 8, 1963 by J. J. Heigl et al provided an automatic viscometer. In the patented device, a system of light sources, each having a corresponding photodetector mounted opposite a light source, was employed for activating electronic equipment in order electronically and accurately to determine the length of time between the passage of the oil meniscus through a first paired light beam-photodetector arrangement, and then through a second paired light beam-photodetector arrangement.

U.S. Pat. No. 3,074,266 patented Jan. 22, 1963 to L. Sadler et al provided an automatic viscosity measurement device in which a float device was used which was responsive to the liquid level in the receiver for the discharge of liquid from a container, to measure and provide a direct reading of the time which elapsed for the rise of the liquid from a first level to a second level in the receiver.

U.S. Pat. No. 3,286,511 patented Nov. 22, 1966 by J. Hankness provided a viscosity measurement device in which a timer was connected to a pair of spaced-apart electrodes in a column through which liquid fell. The timer electrically registered the time interval for the forward end of the liquid stream to transverse the distance between the electrodes.

U.S. Pat. No. 3,604,247 patented Sept. 14, 1971 by P. Gramain et al provided an automatic viscosity meter including a vertical tube in which the liquid whose viscosity was to be measured flowed. The viscosity measurement was obtained by meansuring the time taken by a given volume of liquid to flow between two points. The reading of the passage of three miniscus past these two points was made automatically by using luminous sources and a single receiving element.

U.S. Pat. No. 3,713,328 patented Jan. 30, 1973 by Aritami provided an apparatus for the automatic measurement of viscosity. The timing means was activated by photoelectric devices consisting of pairs of photoelectric cells and light sources in pairs at the upper and lower timing marks of a timing bulb.

U.S. Pat. No. 3,908,441 patented Sept. 30, 1975 by J. M. Virloget provided a device for detaching the level of liquid in a transparent tube, for measuring the viscosity thereof. A radiation source was placed facing a region of the periphery of the tube. A photocell was placed facing a second zone of the tube periphery to receive radiation totally reflected from the internal face of the tube which was wetted by the liquid.

SUMMARY OF THE INVENTION (i) Aims of the Invention

In spite of these patents, there is still a need for an improved erythrocyte settling meter. An object, therefore, of this invention is the provision of an improved erythrocyte settling meter in which the test may be determined rapidly.

Another object of this invention is to provide such meter in the form of a fully automated device.

Yet another object of this invention is to provide such a meter in which precise time is recorded to indicate when the erythrocytes have settled.

(ii) Statement of Invention

This invention provides, in its broadest sense, an improved meter for measuring erythrocyte settling rates, comprising: (a) a base providing a rack adapted to hold an array of tubes at an optimum settling angle; (b) at least one tube to be held in the rack, the tube being adapted to contain a blood sample whose erythrocyte settling rate is to be determined, the tube when in the rack providing an upper window of predetermined length at the upper end thereof, the upper window permitting passage of ambient light therethrough, a lower window of predetermined length adjacent the upper end thereof but below the upper window, the lower window permitting passage of ambient light therethrough, and an opaque section separating the lower window from the upper window; (c) timing means actuated by the passage of light through the windows when the tube contains blood, to determine the erythrocyte settling rate, the timing means comprising (i) an upper photodiode activated by the passage of ambient light through the upper window when the erythrocytes in the blood in the tube settle, to commence cumulative time interval counting representative of the erythrocyte settling rate; and (ii) a lower photodiode activated by the passage of ambient light through the lower window to stop the cumulative time interval counting representative of the erythrocyte settling rate; (d) the erythrocyte settling rate being determined by the exact interval of time which has elapsed between when light passes through the upper window, indicative of the substantial absence of erythrocytes in the area of the upper window, and when light passes through the lower window, indicative of the substantial absence of erythrocytes in the area of the lower window.

(iii) Other Features of the Invention

By one feature of this invention, the meter includes means to display the elapsed time.

By another feature of this invention, the angle is from about 20° to about 70° to the horizontal, preferably about 60° to the horizontal.

By another feature of this invention, the length of each window is about 1 cm in length and the remaining length of the tube is coloured so that ambient light is prevented from passing therethrough.

By a further feature of this invention, a plurality, e.g., about ten such tubes are provided, the tubes having means of clearly differentiating or marking one tube from another, e.g., by making each tube of a different colour.

By another feature of this invention, the upper photodiode is connected to an amplifier and a signal conditioning unit to the start switch of a 0.1 sec. clock gate.

By yet another feature of this invention, the lower photodiode is connected to an amplifier and a signal conditioning unit to the stop switch of a 0.1 sec. clock gate.

By still another feature of this invention, the output of the clock gate is fed to a counter.

By still another feature of this invention, the output of the clock gate is fed to a counter having a display or a printer.

By yet another feature of this invention, the counter is connected to a reset switch, automatically activated by a microswitch when a tube is placed on the rack.

By yet another feature of this invention, the meter includes a bubble level in the base of the rack to assure that the base is level.

(iv) Generalized Description of the Invention

The invention broadly provides for the light activated sensing of the passage of the cell-serum interface past two spaced-apart points in the inclined tube to register the erythrocyte settling rate. The invention provides an erythrocyte rate settling meter which consists of an inclined rack on which a blood test sample tube is placed. The rack has in its base a bubble level to allow the base to be levelled. The inclined rack is fixed at about 60° to the horizontal. Depending on the model, up to ten tubes may be used on the inclined rack at once.

The rack is provided with means to enable the settling rate to be determined. The device includes automatic interval timing means.

The actual time lapse is measured and preferably is recorded by means of a timing circuit. The timing circuit includes an upper photodiode which picks up the light passing through an upper window of the tube and which starts a counting circuit e.g. by being preferably connected to an amplifier and a signal conditioning unit to the start switch of a 0.1 sec. clock gate. When the erythrocytes have settled past the lower window of the tube, light thus passes to a second photodiode, which stops the counting circuit e.g. by being connected to an amplifier and a signal conditioning unit to the stop switch of a 0.1 sec. clock gate. The time lapse is thus accurately shown on display counter.

BRIEF DESCRIPTION OF THE DRAWINGS

In the accompanying drawings,

FIG. 1 is a side elevational view of a simple erythrocyte settling rate meter of the prior art described in U.S. Pat. No. 4,474,056;

FIG. 2 is a top plan view thereof;

FIG. 3 is a simple schematic electrical circuit thereof; and

Figure 4:
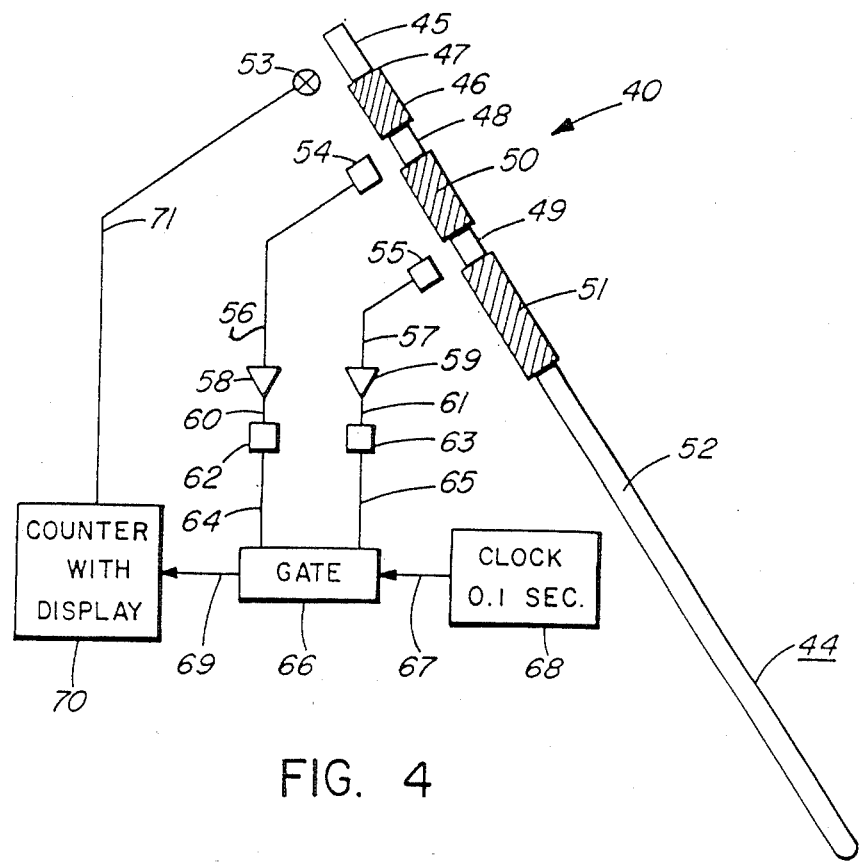
FIG. 4 is a schematic view of the construction and operating details of the erythrocyte settling rate meter of one embodiment of the invention.

DESCRIPTION OF THE ABOVE IDENTIFIED PRIOR ART (i) Description of FIGS. 1 and 2

The device shown consists of a rack 10 including a base 11, a rear upright 12 and a forward foot 13. Preferably, the rack is made from polycarbonate or polymethylmethacrylate sheet. The height of rear upright 12 is such that blood sample tubes 14 are inclined at an angle ($\alpha$) of about 60° to the horizontal.

Near the head 15 of the rack is a clamp and pressure switch 16 coupled to a photocell arrangement 17, to pick up ambient light shining through window 18. A plurality of the blood sample tubes 14 are fixed to the rack by means of the like plurality of clamps and pressure switches 16. The base 11 includes a bubble level 19.

The blood sample tubes 14 have a filling mark. It is imperative that the tube be filled to that mark for good results. About 1 cm of the tube below the mark is clear to provide the window 18 and the rest of the tube is coloured. It is preferred that the tubes have ten different colours.

(ii) Description of FIG. 3

As seen in FIG. 3, which is one embodiment of a circuit arrangement, the photocell 17 has one terminal grounded at 20 and has its other terminal connected to an amplifier 21. The output of the amplifier 21 passes through a diode 22 to a first thermomechanical switch (indicated schematically as block 23) which, when it reaches a predetermined temperature after the passage of a maximum period of time lights the first LED display 24. The circuit also includes a second thermomechanical switch (indicated schematically as block 25) which, when it reaches a predetermined higher temperature than switch 23 after the passage of a longer period of time than the maximum period of time for switch 23 lights second LED display 26. This LED 24 lights up after maximum elapsed time of more than 5 minutes.

A third thermomechanical switch/LED display but of the same structure and operation) is also provided.

DESCRIPTION OF PREFERRED EMBODIMENT (iii) Description of FIG. 4

The embodiment of the invention provided in FIG. 4 is a meter 40 shown schematically as a blood sample tube 44. While not shown, this embodiment would also include a base, a rear upright and a forward foot. Preferably, as in the device described in FIGS. 1 and 2 the rack is made from polycarbonate or polymethylmethacrylate sheet. The height of rear upright is such that blood sample tubes 44 are inclined at an angle ($\alpha$) of about 60° to the horizontal. The blood sample tubes 44 include an upper transparent portion 45 merging with an opaque portion 46 to provide a boundary 47 representative of the full level. Below the opaque portion 46 is a pair of light-transmitting, transparent windows, namely an upper window 48 and a lower window 49 separated by an opaque portion 50. Below lower window 49 is an opaque collar 51 to separate the lower window 49 from the remainder of the transparent tube 44.

As described in the device of the prior art in FIGS. 1 and 2, near the head of the rack is a clamp. In the present embodiment in FIG. 4, there is also a micro-switch switch 53 whose purpose will be described hereinafter.

The rack is also provided with a pair of spaced apart, sensitive photodiodes, namely upper photodiode 54 and a lower photodiode 55. Upper photodiode 54 is adapted to be behind upper window 48, while lower photodiode 55 is adapted to be behind lower window 49.

Upper photodiode 54 is connected, via line 56 to amplifier 58 which is connected, via line 60 to a signal conditioning unit 62 which feeds "start" pulses to a gate 66. Gate 66 is operated by pulses fed via line 67 from a 0.1 sec. clock 68. The output from gate 66 is fed via line 69 to a counter 70 provided with a display.

Lower photodiode 55 is connected via line 57 to amplifier 59 which is connected, via line 61 to a signal conditioning unit 63 which feeds "stop" pulses to gate 66. Thus the counting is started in counter 70 upon receiving signals from signal conditioning unit 62, and is stopped upon receiving signals from signal conditioning unit 63.

Counter 70 is connected, via line 71 to microswitch 53 which automatically clears counter 70 when the blood sample tube is clamped or otherwise placed on the rack.

OPERATION OF PRIOR ART DEVICE (i) Operation of FIGS. 1-3

In operation, clamping the blood sample tubes 14 into the rack 10 opens the circuit to the LED displays (24,26) from the photocell. As the erythrocytes settle, the clear plasma allows the ambient light shining through window 18 to activate the photocell voltage. This is amplified at amplifier 21, passes through the diode 22 and begins to warm the first thermomechanical switch 23. Thermomechanical switch 23 is of a conventional construction well-known in the art. It has an internal construction including resistive elements enabling it to complete the circuit to the photocell 17 and thus to be heated. Thermomechanical switch 23, after reaching a preset temperature, dependent on the magnitude of the current originating at the photocell 17, which, in turn is dependent on the amount of light impinging on the photocell 17, completes a circuit to a first LED display 24, thereby lighting display 24. The maximum time required to complete the circuit in the first LED 24 is when the current is at a minimum, which, in one embodiment is five minutes. This is indicative of a minimum amount of light impinging on the photocell when erythrocytes are present at the area of the window. The minimum time required to complete the circuit to the first LED 24 is when the current is at a maximum, which would be less than five minutes. This is indicative of a maximum amount of light impinging on the photocell 17 when substantially no erythrocytes are present at the area of the window. The circuit including photocell 17, amplifier 21, diode 22 and first thermomechanical switch 23 also includes a second thermomechanical switch shown schematically at 25. Thermomechanical switch 25 also has an internal construction, e.g. resistive elements enabling it to complete the circuit to the photocell 17 and thus to be heated. Thermomechanical switch 25 after reaching a preset higher temperature than that of first thermomechanical switch 23, and which is dependent on the magnitude of the current originating at the photocell 17, which, in turn is dependent on the amount of light impinging on the photocell 17, completes a circuit to the second LED display 26, thereby lighting display 26.

This circuit supplies insufficient current to warm the thermomechanical switch 23 sufficiently to light the LED display 24 if sedimentation is not fast enough so that the length of the window monitored by the photocell is clear. As described above, whether LED 24 is lit or not, the photocell current passes through the second thermomechanical switch 25, which when it heats up sufficiently after the lapse of an additional period of time lights another LED and so to the third LED (not shown). If the instrument is started and left for a long time, all three LED's will be lit, but if looked at in five minutes, when, as described above, only LED 24 will be lit, the blood can be judged abnormal.

The sedimentation rate of the erythrocytes (blood cells) is very different in the inclined position compared to the ordinary vertical settling position.

OPERATION OF PREFERRED EMBODIMENT (i) Description of Operation of FIG. 4

In operation, clamping the blood sample tubes 44 into the rack clears the counter 70. As the erythrocytes settle, the clear plasma allows the ambient light shining through upper window 48 to start the counter 70 in the manner described above. As the erythrocytes settle still more, the clear plasma allows the ambient light shining through lower window 49 to stop the counter 70 in the manner described above. The time displayed on counter 70 is representative of the settling rate.

The opaque segments 46, 50 on the glass tube should be of the order of about 10 mm long, with a window 48, 49 about 3-4 mm long for each of of the two photodiodes. The opaque segments of the tube could be colour-coded to assist identification. Alternatively, the current clear ESR tubes could be used if the device was fitted with metal or opaque (black) plastic tubes in the rack to provide similar opaque and clear segments when a clear glass tube was placed in the device.

It is preferred that the photodiodes be those known by the Trade Mark, PHOTODARLINGTON, or similarly light-sensitive units, each feeding the signal to the amplifiers 58, 59 and signal-conditioning units 62, 63, and thence to a gate 66. The signal from the upper photodiode 54 serves to start the counter 70 operated by an electronic gate 66 fed with signals from a quartz clock 68 of 0.1 second accuracy. As the settled interface clears the second window 49 the lower photodiode 55 stops the clock and gives the time for the settling distance between the two windows 48, 49. Thus, exact tube filling level is not critical to the result, although filling should be relatively consistent, say to the top of the upper opaque portion of the tube, for good reproduceability.

The time signal recorded on the counter 70 remains in place, even when measured tube 44 is removed from the device 40. However, each counter is automatically reset when a new filled tube 44 is placed in the device 40, when it presses onto the microswitch 53 located at the top of each tube position. In this way, confusion as to whether the counter has or has not been reset is avoided. Meanwhile, the readings on, or the progress of, all other counters continue, unaffected.

A separate display is preferred for each tube location to reduce confusion and chances of errors of association. This provides increased convenience and reduced risk of error.

Light emitting diode (LED) displays (4, or 5 digits if tenths are to show) are preferred for their clear visibility in a variety of light conditions and the wider viewing angles permitted. Liquid crystal displays have to be larger, for equivalent reading clarity, have only a narrow viewing angle (ca. 20°) and are difficult to read under poor lighting conditions.

EXAMPLE (i) Experimental Results Using Device of FIGS. 1-3

In the standard vertical test, it requires 60 minutes to settle 3 mm for normal blood and abnormal-to-abnormal ratios can be read up to 18 with settled distances of up to 55 mm. In the inclined settler, the normal blood settled 4 mm in ten minutes and ratios of abnormal-to-normal reached 19 and settled distances of 77 mm. In five minutes only, very often useful differentiation is possible (see tables below).

| Standard E.S.R. test | | Inclined E.S.R. test | |
| --- | --- | --- | --- |
| Settled distance, mm (60 min) | Ratio, abnormal/ slow normal | Settled distance, mm (10 min) | Ratio, abnormal/ slow normal |
| 3 | 1.0 | 4 | 1.0 |
| 4 | 1.3 | 14 | 3.5 |
| 6 | 2.0 | 22 | 5.5 |
| 10 | 3.3 | 26 | 6.5 |
| 15 | 5.0 | 34 | 8.5 |
| 22 | 7.3 | 38 | 9.5 |
| 23 | 7.7 | 39 | 9.8 |
| 27 | 9.0 | 60 | 15.0 |
| 46 | 15.3 | 72 | 18.0 |
| 55 | 18.3 | 77 | 19.3 |

| Settled distance, mm (60 min) | Ratio, abnormal/ 4 mm normal | Ratio, abnormal/ 3 mm normal | Settled distance, mm (5 min) | Ratio, abnormal/ 4 mm normal | Settled distance, mm (15 min) | Ratio, abnormal/ 3 mm normal |
| --- | --- | --- | --- | --- | --- | --- |
| 3 | — | 1.0 | 0 | — | 24 | 1.0 |
| 4 | 1.0 | 1.3 | 0.5 | 1 | 28 | 1.2 |
| 6 | 1.5 | 2.0 | 3 | 6 | 38 | 1.6 |
| 10 | 2.5 | 3.3 | 4 | 8 | 42 | 1.8 |
| 15 | 3.8 | 5.0 | 10 | 20 | 59 | 2.5 |
| 22 | 5.5 | 7.3 | 9 | 18 | 56 | 2.3 |
| 23 | 5.8 | 7.7 | 9 | 18 | 55 | 2.3 |
| 27 | 6.8 | 9.0 | 6 | 12 | 88 | 3.7 |
| 46 | 11.5 | 15.3 | 19 | 38 | 95 | 4.0 |

| Standard E.S.R. test | | | Inclined E.S.R. test | | |
|---|---|---|---|---|---|
| 55 | 13.8 | 18.3 | 23 | 46 | 98 | 4.1 |

(ii) Component Parts for Embodiment of FIG. 4

While it is not desired to be restricted to any particular components, the following is a general parts list, for a 10 tube apparatus:

20-PHOTODARLINGTON (or equiv.) photodiodes
10-4, or 5 digit (with decimal) light emitting diodes (e.g. 0.25" Hewlett-Packard type)
10-standard, start-stop TTL or CMOS gates
10-resetting, pressure-sensitive micro-switches
1-power supply, appropriate for local line voltage (may be battery-operated for a doctor's office, 1-tube unit, to reduce cost)

SUMMARY

The present invention will allow a determination to be made in 5 to 15 minutes. A doctor (or probably his nurse) can perform the test while continuing the examination of the patient and have the results in time for diagnosis.

The system would also be of great assistance during natural disasters. For example, during flooding, distressed people will appear who are suffering from no disease, just exposure, hunger, anxiety, etc., but there will be those who have drunk contaminated water and are suffering from water-borne diseases. Those with a disease can, with the aid of the erythrocyte settling meter of aspects of this invention, be quickly separated.

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

We claim:

1. A meter for measuring erythrocyte settling rates, comprising:
   (a) a base providing a rack adapted to hold an array of tubes at an optimum settling angle;
   (b) at least one tube to be held in said rack, said tube being adapted to contain a blood sample whose erythrocyte settling rate is to be determined, said tube wehn in said rack providing an upper window of predetermined length at the upper end thereof, said upper window permitting passage of ambient light therethrough, a lower window of predetermined length adjacent the upper end thereof but below said upper window, said lower window permitting passage of ambient light therethrough, and an opaque section separating said lower window from said upper window;
   (c) timing means actuated by the passage of ambient light through said windows when said tube contains blood, to determine the erythrocyte settling rate, said timing means comprising
      (i) an upper photodiode activated by the passage of ambient light through said upper window when the erythrocytes in the blood in said tube settle, to commence cumulative time interval counting representative of the erythrocyte settling rate; and
      (ii) a lower photodiode activated by the passage of ambient light through said lower window to stop the cumulative time interval counting representative of the erythrocyte settling rate;
   said erytyrocyte settling rate being determined by the exact interval of time which has elapsed between when ambient light passes through said upper window, indicative of the substantial absence of erythrocytes in the area of said upper window, and when ambient light passes through said lower window, indicative of the substantial absence of erythrocytes in the area of said lower window.

2. The meter as claimed in claim 1 including (d) means to display said elapsed time.

3. The meter of claim 1 wherein said angle is from about 20° to about 70° to the horizontal.

4. The meter of claim 3 wherein said angle is about 60° to the horizontal.

5. The meter of claim 1 wherein the remainder to each said tube is coloured so that ambient light is prevented from passing therethrough.

6. The meter of claim 5 wherein each said upper window and said lower window is about 1 cm in length.

7. The meter of claim 5 wherein a plurality of such tubes are provided, said tubes having means of clearly differentiating or marking one tube from another.

8. The meter of claim 7 wherein each tube is of different colour.

9. The meter of claim 7 wherein ten such tubes are provided.

10. The improved meter of claim 1 wherein said upper photodiode is connected to an amplifier and a signal conditioning unit to the start switch of a 0.1 sec. clock gate.

11. The improved meter of claim 1 wherein said lower photodiode is connected to an amplifier and a signal conditioning unit to the stop switch of a 0.1 sec. clock gate.

12. The improved meter of claim 10 wherein said lower photodiode is connected to an amplifier and a signal conditioning unit to the stop switch of a 0.1 sec. clock gate.

13. The improved meter of claim 12 wherein the output of the clock gate is fed to a counter.

14. The improved meter of claim 12 wherein the output of the clock gate is fed to a counter having a display or a printer.

15. The improved meter of claim 12 wherein said counter is connected to a reset switch, automatically activated by a microswitch when a tube is placed on the rack.

16. The improved meter of claim 1 including a bubble level in the base of the rack to assure that the base is level.

* * * * *

UNITED STATES PATENT AND TRADEMARK OFFICE
CERTIFICATE OF CORRECTION

PATENT NO. : 4,566,315
DATED : January 28, 1986
INVENTOR(S) : O'Brien et al

It is certified that error appears in the above-identified patent and that said Letters Patent is hereby corrected as shown below:

Column 8, line 43, change "in" to --to--.

Column 12, line 14, before "said" insert --(d)--.

Column 12, line 28, change "to" to --of--.

Signed and Sealed this

Thirteenth Day of May 1986

[SEAL]

Attest:

Attesting Officer

DONALD J. QUIGG

Commissioner of Patents and Trademarks